United States Patent [19]

D'Silva

[11] 4,303,669

[45] Dec. 1, 1981

[54] HYBRID 1,3-DIONE-CARBAMATE COMPOUNDS

[75] Inventor: Themistocles D. J. D'Silva, South Charleston, W. Va.

[73] Assignee: Union Carbide Corporation, New York, N.Y.

[21] Appl. No.: 133,750

[22] Filed: Mar. 25, 1980

[51] Int. Cl.³ .................. A01N 43/16; A01N 43/08; C07D 317/44; C07D 307/77
[52] U.S. Cl. .......................... 424/282; 260/340.5 R; 260/340.9 R; 260/346.22; 260/456 NS; 260/456 R; 260/465 D; 260/465.4; 260/453.3; 544/58.2; 548/182; 549/14; 549/30; 549/37; 549/38; 549/55; 549/63; 560/135; 560/136; 560/137; 560/148; 560/153; 424/244; 424/246; 424/248.5; 424/270; 424/275; 424/277; 424/278; 424/285; 424/300

[58] Field of Search ......... 260/465.4, 465 D, 340.9 R, 260/340.5 R, 346.22, 456 R, 456 NS; 560/148, 135, 136, 137; 544/58.2; 424/282, 278, 300

[56] References Cited

U.S. PATENT DOCUMENTS

| | | | |
|---|---|---|---|
| 3,812,174 | 5/1974 | Brown et al. | 560/137 |
| 4,169,894 | 10/1979 | D'Silva | 560/136 |
| 4,179,514 | 12/1979 | D'Silva | 544/58.2 |
| 4,209,532 | 6/1980 | Wheeler | 260/465 D |

*Primary Examiner*—Ethel G. Love
*Attorney, Agent, or Firm*—Clement J. Vicari; William R. Moran

[57] ABSTRACT

Novel hybrid 1,3-dione-carbamate compounds which exhibit utility as insecticides and acaricides. Also included are insecticidal and acaricidal compositions containing these compounds and a method of controlling insects and acarids.

48 Claims, No Drawings

HYBRID 1,3-DIONE-CARBAMATE COMPOUNDS

This invention relates to novel hybrid 1,3-dione-carbamate compounds and methods of preparing same. This invention is also directed to a composition comprising an acceptable carrier and a pesticidally effective amount of a compound of this invention, as well as to a method of controlling pests which comprises subjecting the pests to a pesticidally effective amount of a compound of this invention.

More particularly, this invention relates to compounds of the formula:

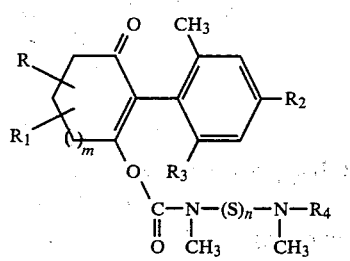

wherein:
m=0 or 1;
n=1 or 2;
R, $R_1$, $R_2$, and $R_3$ are individually hydrogen or alkyl groups of one to four carbon atoms;
$R_4$ is:
(a) fluorocarbonyl or
(b) a group of the formula:

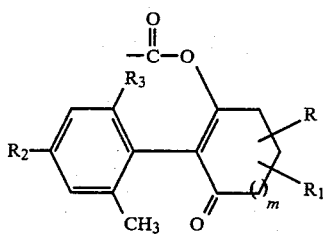

A.

wherein R, $R_1$, $R_2$, $R_3$ and m have the above indicated values;

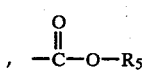

B.

wherein $R_5$ is:
(1) a phenyl group which is unsubstituted or substituted with one or more $C_1$-$C_{12}$ alkyl, chloro, fluoro, bromo, alkoxy, alkylthio, alkylthioalkyl, alkylsulfinyl, alkylsulfinylalkyl, alkylsulfonyl, alkylsulfonylalkyl, alkynyloxy, dialkylamino, alkoxyamino, formamidino, cyano, dioxolanyl or dithiolanyl group in any combination; or
(2) a naphthyl, tetrahydronaphthyl, dihydrobenzofuranyl, benzodioxalanyl, or benzothienyl group, all of which is unsubstituted or substituted with one or more alkyl groups; or
(3) a group of the formula:

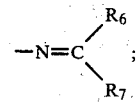

wherein $R_6$ is a chloro, alkyl, alkylthio, cyanoalkylthio, amidoalkylthio or cyano group; or $R_6$ is hydrogen provided $R_7$ is not hydrogen;
$R_7$ is an alkyl, alkylthio, alkoxycarbonyl, aminocarbonyl, alkylaminocarbonyl, dialkylaminocarbonyl, alkylthioalkyl, cyanoalkyl, alkylsulfinylalkyl, alkylsulfonylalkyl, alkoxyalkyl, nitroalkyl, hydroxyalkyl, or phenyl group, said phenyl group is unsubstituted or substituted with one or more alkyl, chloro, or fluoro groups in any combination; or $R_7$ is hydrogen, provided $R_6$ is not hydrogen; or
(4) cyclic oximes selected from the group consisting of 2-oximino-1,4-dithianes, 2-oximino-1,3-dithianes, 4-oximino-1,3-dithiolanes, 2-oximino-1,4-dioxanes, 2-oximino-tetrahydro-1,4-thiazine-3-ones, 2-oximino-1,3-dithiolanes, 2-imino-4-oximino-1,3-dithiolanes, 3-oximinothiophanes, 2-oximinothiophanes, 2-oximino-tetrahydro-1,4-oxazine-3-ones, 2-oximino-1,4-oxathianes, 4-oximino-1,3-oxathiolanes, 2-oximino-thiazolidin-3-ones, 2-oximino-1,3-thiazolidin-4-ones or 2-oximino-tetrahydro-1,4-thiazin-5-ones, each of which is unsubstituted or substituted with one to four alkyl groups and in the said preferred ring structures sulfur can be in any of its oxidation states.

Compositions falling within the above generic formula exhibit biological activity as acaricides or insecticides to a greater or lesser extent. Some exhibit very powerful activity in extremely small dosages while others require larger dosages to be effective.

In general, the compounds which are preferred for acaricidal or insecticidal activity are those of the above generic structural formula wherein R, $R_1$, $R_2$ and $R_3$ are hydrogen, methyl and isopropyl; $R_6$ is hydrogen, lower alkyl, alkylthio; $R_7$ is lower alkyl, alkylthioalkyl, cyanoalkyl, alkylsulfonylalkyl.

Compounds which are most preferred are those in which m=1, the R and $R_1$ constituents are in the fifth position of the cyclohexanedione and wherein $R_3$ is hydrogen as shown in the following formula:

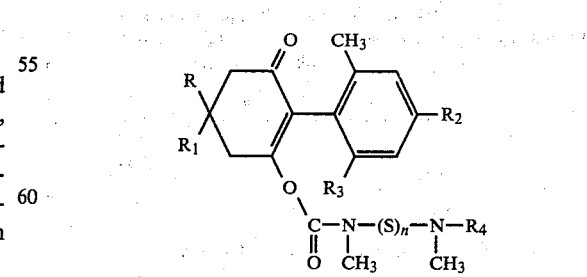

wherein $R_3$ is hydrogen and R, $R_1$, $R_2$, $R_4$ and n have the above indicated value.

Some of the preferred compounds are represented by structure and nomenclature as follows:

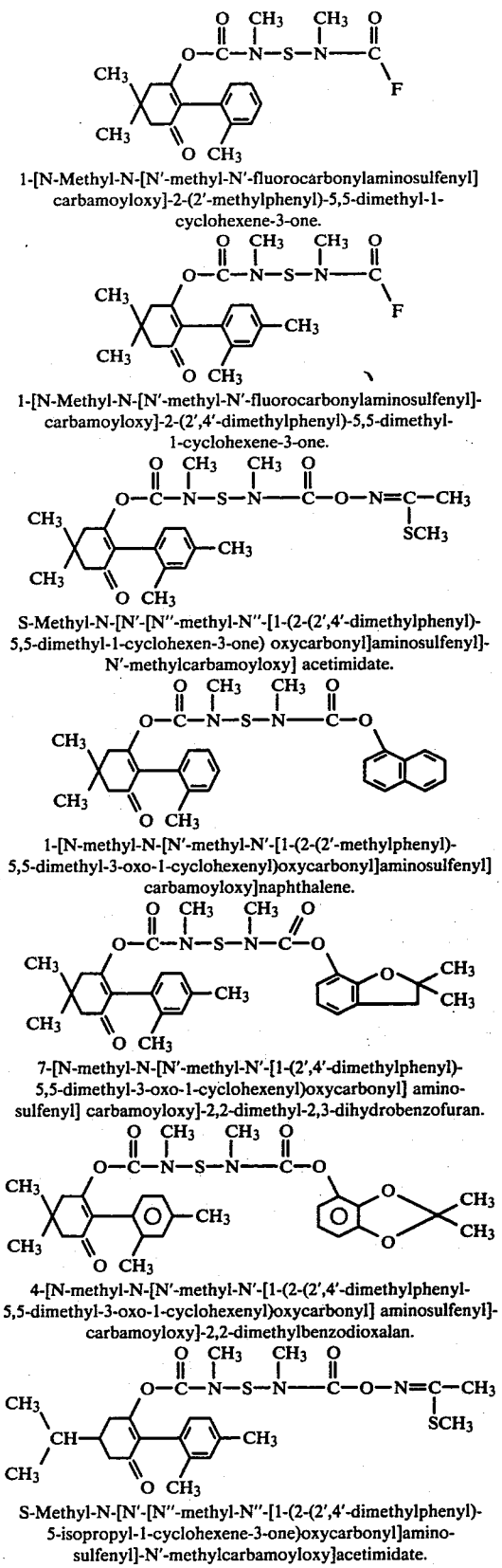

1-[N-Methyl-N-[N'-methyl-N'-fluorocarbonylaminosulfenyl]carbamoyloxy]-2-(2'-methylphenyl)-5,5-dimethyl-1-cyclohexene-3-one.

1-[N-Methyl-N-[N'-methyl-N'-fluorocarbonylaminosulfenyl]-carbamoyloxy]-2-(2',4'-dimethylphenyl)-5,5-dimethyl-1-cyclohexene-3-one.

S-Methyl-N-[N'-[N''-methyl-N''-[1-(2-(2',4'-dimethylphenyl)-5,5-dimethyl-1-cyclohexen-3-one)oxycarbonyl]aminosulfenyl]-N'-methylcarbamoyloxy] acetimidate.

1-[N-methyl-N-[N'-methyl-N'-[1-(2-(2'-methylphenyl)-5,5-dimethyl-3-oxo-1-cyclohexenyl)oxycarbonyl]aminosulfenyl]carbamoyloxy]naphthalene.

7-[N-methyl-N-[N'-methyl-N'-[1-(2',4'-dimethylphenyl)-5,5-dimethyl-3-oxo-1-cyclohexenyl)oxycarbonyl] aminosulfenyl] carbamoyloxy]-2,2-dimethyl-2,3-dihydrobenzofuran.

4-[N-methyl-N-[N'-methyl-N'-[1-(2-(2',4'-dimethylphenyl-5,5-dimethyl-3-oxo-1-cyclohexenyl)oxycarbonyl] aminosulfenyl]-carbamoyloxy]-2,2-dimethylbenzodioxalan.

S-Methyl-N-[N'-[N''-methyl-N''-[1-(2-(2',4'-dimethylphenyl)-5-isopropyl-1-cyclohexene-3-one)oxycarbonyl]aminosulfenyl]-N'-methylcarbamoyloxy]acetimidate.

In general, the novel compounds of this invention can be prepared according to several methods illustrated by the following reaction schemes.

Method I

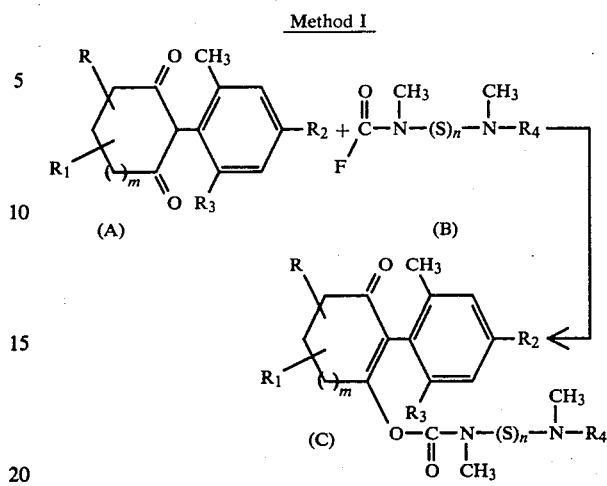

wherein $R-R_4$, m and n are as indicated previously.

Method I is a reaction scheme that can be used to make any compound of the instant invention.

Method II

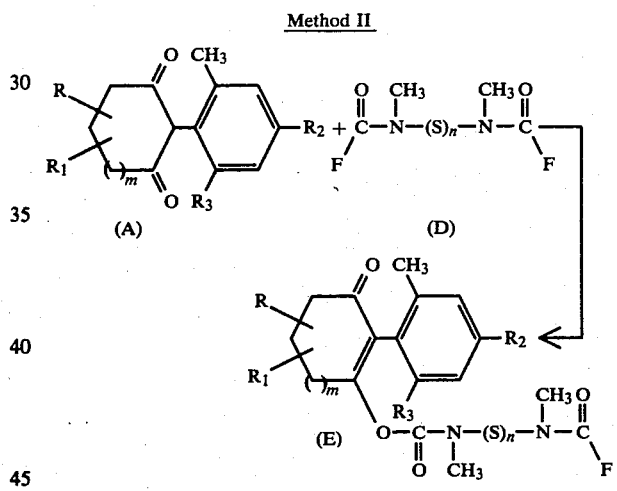

Method II is limited to compounds wherein $R_4$ is

(fluorocarbonyl) or—

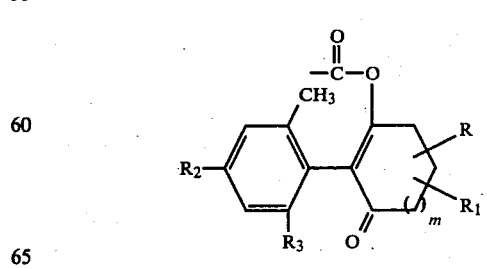

Method III

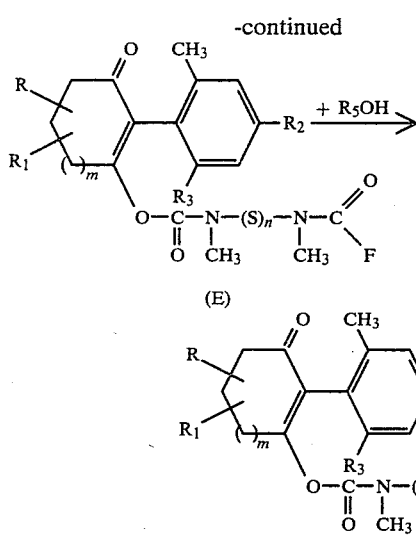

(E)

$$\text{structure with } O-C(=O)-N(CH_3)-(S)_n-N(CH_3)-C(=O)-OR_5$$

The reactions in Methods I, II and III are conducted in the presence of an acid acceptor, preferably in an inert solvent. Substantially equivalent amounts of an acid acceptor and the reactants are used although a slight excess of the acid acceptor can be used if desired. In Method II, when a symmetrical bis-carbamate sulfide or disulfide is desired, the reaction can be carried out by using two equivalents of the dione compound (A) with one equivalent of the carbamoyl fluoride compound (B) and two equivalents of the acid acceptor. The synthesis of these symmetrical compounds also can be accomplished in two steps. The first step consists of the reaction depicted in the reaction scheme of Method II above. The second step consists of reacting the reaction product of Method II, compound (E), with the second equivalent of the dione compound (A) and the acid acceptor.

It should also be noted that although compound (E), above, the product of Method II, is itself a pesticidal compound of the instant invention, it is also capable of use as a reactant intermediate in the synthesis of compounds according to Method III, above.

The acid acceptor utilized in the reactions of Methods I, II and III can be either an organic or an inorganic base. Illustrative of organic bases are tertiary amines such as trimethylamine, triethylamine, pyridine, isoquinoline or 1,4-diazabicyclo[2.2.2]octane; or alkali metal alkoxides, as for example, sodium methoxide, sodium ethoxide, or the like. Bases such as sodium carbonate, sodium hydroxide or potassium hydroxide are illustrative of inorganic bases that are useful as acid acceptors.

The reactions in Methods I to III can be conducted in organic solvents, in an aqueous solvent or in a two-phase mixture of organic and aqueous solvents. When an inorganic base is used in a heterogeneous phase system or a homogeneous system, a phase transfer agent such as quaternary ammonium halides or crown-ether compounds can be used to facilitate the transfer of the reactants across the phase interface or to improve the nucleophilicity of the dione, phenol or oxime compound.

The dione compounds, reactant (A) above can be prepared according to the method described in U.S. Pat. No. 4,175,135 issued on Nov. 20, 1979.

The following acaricidally or insecticidally active compounds are illustrative of compounds within the purview of the above generic formula and which can be conveniently prepared by the process of this invention simply by selecting appropriate reactants for use in the procedures described below.

4-[N-methyl-N-[N'-methyl-N'-[1-(2-(2'-methylphenyl)-5,5-dimethyl-3-oxo-1-cyclohexenyl)oxycarbonyl]aminosulfenyl]carbamoyloxy]benzothiophene.

1-[N-methyl-N-[N'-methyl-N'-[1-(2-(2'-methylphenyl)-5,5-dimethyl-3-oxo-1-cyclohexenyl)oxycarbonyl]aminosulfenyl]carbamoyloxy]-2-ethylthiomethylbenzene.

1-[N-methyl-N-[N'-methyl-N'-[1-(2-(2'-methylphenyl)-5,5-dimethyl-3-oxo-1-cyclohexenyl)oxycarbonyl]aminosulfenyl]carbamoyloxy]-2-propynyloxybenzene.

1-[N-methyl-N[N'-methyl-N'-[1-(2-(2'-methylphenyl-5,5-dimethyl-3-oxo-1-cyclohexenyl)oxycarbonyl]aminosulfenyl]carbamoyloxy]-3-methyl-4-dimethylformamidinobenzene.

1-[N-methyl-N-[N'-methyl-N'-[1-(2(2'-methylphenyl)-5,5-dimethyl-3-oxo-1-cyclohexenyl)oxycarbonyl]aminosulfenyl]carbamoyloxy]-3,5-dimethyl-4-dimethylaminobenzene 1-[N-methyl-N-[N'-methyl-N'-[1-(2-(2'-methylphenyl)-5,5-dimethyl-3-oxo-1-cyclohexenyl)oxycarbonyl aminosulfenyl]carbamoyloxy]-2-bromo-4-cyanobenzene.

1-[N-methyl-N-[N'-methyl-N'-[1-(2-(2'-methylphenyl)-5,5-dimethyl-3-oxo-1-cyclohexenyl)oxycarbonyl]aminothiosulfenyl]carbamoyloxy]-2-(1,3-dioxolan-2-yl)benzene.

1-[N-methyl-N-[N'-methyl-N'-[1-(2-(2'-methylphenyl)-4,5-dimethyl-3-oxo-1-cyclopentenyl)oxycarbonyl]aminosulfenyl]carbamoyloxy]-3-methyl-4-nitrobenzene.

S-methyl-N-[N'-[N''-methyl-N''-[1-(2-(2'-methylphenyl)-5,5-dimethyl-3-oxo-1-cyclohexenyl)oxycarbonyl]aminosulfenyl]N'-methylcarbomoyloxy]acetimidate.

[N-methyl-N-[N'-methyl-N'-[1-(2-(2'-methylphenyl)-5,5-dimethyl-3-oxo-1-cyclohexenyl)oxycarbonyl]aminosulfenyl]carbamoyloximino]-2-methyl-2-methylthiopropionaldehyde.

[N-methyl-N-[N'-methyl-N'-[1-(2-(2'-methylphenyl)-5,5-dimethyl-3-oxo-1-cyclohexenyl)oxycarbonyl]aminosulfenyl]carbamoyloximino]-2-methyl-2-nitropropionaldehyde.

S-methyl-N-[N'-methyl-N'-[N''-methyl-N''-[1-(2-(2'-methylphenyl)-5,5-dimethyl-3-oxo-1-cyclohexenyl)oxycarbonyl]aminosulfenyl]carbamoyloxy]-N''',N'''-dimethyl oxamimidate.

S-methylcarbamoyl-N-[N'-methyl-N'-[N''-methyl-N''[1-(2-(2'-methylphenyl)-5,5-dimethyl-3-oxo-1-cyclohexenyl)oxycarbonyl]aminosulfenyl]carbamoyloxy]acetimidate.

4-[N-methyl-N-[N'-methyl-N'-[1-(2-(2'-methylphenyl)-5,5-dimethyl-3-oxo-1-cyclohexeneyl)oxycarbonyl]aminosulfenyl]carbamoyloximino]-5,5-dimethyl-1,3-dithiolane.

5-[N-methyl-N-[N'-methyl-N'[1-(2-(2'-methylphenyl)-5,5-dimethyl-3-oxo-1-cyclohexenyl)oxycarbonyl]aminosulfenyl]carbamoyloximino]-4-methyl-1,3-oxathiolane.

5-[N-methyl-N-[N'-methyl-N'-[1-(2-(2'-methylphenyl)-5,5-dimethyl-3-oxo-1-cyclohexenyl)oxycarbonyl]aminothiosulfenyl]carbamoyloximino]-2,2,3-trimethyl-thiazolidin-4-one.

2-[N-methyl-N-[N'-methyl-N'-[1-(2-(2'-methylphenyl)-5,5-dimethyl-3-oxo-1-cyclohexenyl)oxycarbonyl]aminosulfenyl]carbamoyloximino]-3,3-dimethyl-1-methylthiobutanone.

2-[N-methyl-N-[N'-methyl-N'-[1-(2-(2'methylphenyl)-5,5-dimethyl-3-oxo-1-cyclohexenyl)oxycarbonyl]aminosulfenyl]carbamoyloximino]-3-methylsulfonylbutanone.

[N-methyl-N-[N'-methyl-N'-[1-(2-(2'-methylphenyl)-5,5-dimethyl-3-oxo-1-cyclohexenyl)oxycarbonyl]aminosulfenyl]carbamoyloximino]-2,2-dimethyl-4-cyanobutyraldehyde.

2-[N-methyl-N-[N'methyl-N'-[1-(2-(2'-methylphenyl)-5,5-dimethyl-3-oxo-1-cyclohexenyl)oxycarbonyl]aminosulfenyl]carbamoyloximino]-4-methyltetrahydrothiazine-3-one.

2-[N-methyl-N-[N'-methyl-[1-(2-(2'-methylphenyl)-5,5-dimethyl-3-oxo-1-cyclohexenyl)oxycarbonyl]aminosulfenyl]carbamoyloximino]-3,3-dimethylthiophane.

2-[N-methyl-N-[N'-methyl-N'-[1-(2-(2'-methylphenyl)-5,5-dimethyl-3-oxo-1-cyclohexenyl)oxycarbonyl]aminosulfenyl]carbamoyloximino]-1,3-dithiolane.

4-[N-methyl-N-[N'-methyl-N'-[1-(2-(2'-methylphenyl)-5,5-dimethyl-3-oxo-1-cyclohexenyl)oxycarbonyl]aminosulfenyl]carbamoyloximino]-5,5-dimethyl-2-methylimino-1,3-dithiolane.

3-[N-methyl-N-[N'-methyl-N'-[1-(2-(2-methylphenyl)-5,5-dimethyl-3-oxo-1-cyclohexenyl)oxycarbonyl]aminosulfenyl]carbamoyloximino]-2,2-dimethyl-1,4-dioxane.

2-[N-methyl-N-[N'-methyl-N'-[1-(2-(2-methylphenyl)-5,5-dimethyl-3-oxo-1-cyclohexenyl)oxycarbonyl]aminosulfenyl]carbamoyloximino]-3-isopropyl-1,3-thiazolidin-4-one.

1-[N-methyl-N-[N'-methyl-N'-[1-(2-(2',4'-dimethylphenyl)-4-methyl-3-oxo-1-cyclopentenyl) oxycarbonyl] aminosulfenyl carbamoyloxy]-3-methyl-4-nitrobenzene.

1-[N-methyl-N-[N'-methyl-N'-[1-(2-(2'-methylphenyl)-3-oxo-1-cyclohexenyl)oxycarbonyl] aminothiosulfenyl]carbamoyloxy]naphthalene.

1-[N-methyl-N-[N'-methyl-N'-[1-(2-(2'-methylphenyl)-5-butyl-3-oxo-1-cyclohexenyl) oxycarbonyl]aminosulfenyl] carbamoyloxy]-4-dodecylbenzene.

7-[N-methyl-N-[N'-methyl-N'-[1-(2-(2',4'-dimethylphenyl)-5-isopropyl-3-oxo-1-cyclohexenyl) oxycarbonyl] aminosulfenyl] carbamoyloxy]-2,2-dimethyl-2,3-dihydrobenzofuran.

7-[N-methyl-N-[N'-methyl-N'-[1-(2-(2'-methylphenyl)-5,5-dimethyl-3-oxo-1-cyclohexenyl) oxycarbonyl] aminosulfenyl] carbamoyloxy]-2,2-dimethyl-2,3-dihydrobenzofuran.

1-[N-methyl-N-[N'-methyl-N'-[1-(2-(2'-methylphenyl)-5,5-dimethyl-3-oxo-1-cyclohexene)oxycarbonyl] aminosulfenyl] carbamoyloxy] naphthalene.

4-[N-methyl-N-[N'-methyl-N'-[1-(2-(2',4'-dimethylphenyl)-5,5-dimethyl-3-oxo-1-cyclohexenyl) oxycarbonyl] aminosulfenyl] carbamoyloxy]-2,2-dimethylbenzodioxalan.

7-[N-methyl-N-[N-'-methyl-N'-[1-(2-(2',4'-dimethylphenyl)-5,5-dimethyl-3-oxo-1-cyclohexenyl)oxycarbonyl] aminosulfenyl] carbamoyloxy]-2,2-dimethyl-2,3-dihydrobenzofuran.

S-Methyl-N-[N'-[N''-methyl-N''-[1-(2-(2',4'-dimethylphenyl-5-isopropyl-1-cyclohexenyl-3-one)oxycarbonyl]aminosulfenyl]-N'-methylcarbamoyloxy] acetimidate.

The following examples will more fully illustrate the present invention. At the beginning of some of the examples is an indication of the generally described method utilized to prepare the compounds.

EXAMPLE 1

Preparation of 1-[N-Methyl-N-[N'-methyl-N'-fluorocarbonylaminosulfenyl] carbamoyloxy]-2-(2'-methylphenyl)-5,5-dimethyl-1-cyclohexene-3-one. (Method II)

To a solution of 1.52 g. (0.01 m) of bis-(N-methyl-N-fluorocarbonylamino) sulfide and 1.01 g. (0.01 m) of triethylamine in 100 ml of toluene was added drop wise with stirring 2.3 g (0.01 m) of 2-(2-methylphenyl)-5,5-dimethylcyclohexan-1,3-dione dissolved in toluene and methylene chloride. After the reaction mixture was stirred at ambient temperature for 20 hours it was washed successively with dilute sodium carbonate solution and with water until the wash was neutral. The organic phase was dried over anhydrous sodium sulfate and concentrated to afford 3.18 g of pale yellow oil. Trituration with isopropyl ether and cooling afforded 1.18 g of a white solid. m.p. 103°–104° C.

Calc'd for $C_{19}H_{23}FN_2O_4S$: C, 57.85; H, 5.87; N, 7.10; Found: C, 58.14; H, 5.94; N, 7.13

EXAMPLE 2

Preparation of 1-[N-Methyl-N-[N'-methyl-N'-fluorocarbonylaminosulfenyl]carbamoyloxy]-2-(2',4'-dimethylphenyl)-5,5-dimethyl-1-cyclohexene-3-one. (Method II)

To a solution of 7.6 g (0.05 m) of bis-(N-methyl-N-fluorocarbonylamino) sulfide in 400 ml of toluene was added with cooling and stirring a solution of 12.21 g (0.05 m) of 2-(2,4-dimethylphenyl)-5,5-dimethylcyclohexan-1,3-dione dissolved in 150 ml of methylene chloride and 5.05 g (0.05 m) of triethylamine. The addition was carried over a period of 0.5 hour. After stirring the reaction mixture for an additional period of two hours, it was washed with 5 percent sodium carbonate solution and then with water until neutral. The organic phase was dried over anhydrous magnesium sulfate, filtered and concentrated under reduced pressure to afford 10.5 g of a viscous oil. The crude product was purified by chromatographic method.

Calc'd for $C_{20}H_{25}FN_2O_4S$: C, 58.81; H, 6.17; N, 6.86; Found: C, 59.56; H, 6.23; N, 7.07

EXAMPLE 3

Preparation S-Methyl-N-[N'-[N''-methyl-N''-[1-(2-(2',4'-dimethylphenyl)-5,5-dimethyl-1-cyclohexene-3-one) oxycarbonyl]aminosulfenyl]-N'-methylcarbamoyloxy] acetimidate. (Method I)

To a suspension of 2.0 g (0.0082 m) of 2-(2,4-dimethylphenyl)-5,5-dimethylcyclohexan-1,3-dione in 100 ml of toluene was added 2.21 g (0.0082 m) of S-methyl-N[N'-methyl-N'-[N''-fluorocarbonyl-N''-methylaminosulfenyl] carbamoyloxy] thioacetimidate followed by dropwise addition of 0.83 g (0.0082 m) of triethylamine. Methylene chloride (5 ml) was added to obtain a homogeneous solution. After stirring at room temperature for four days and at 50° C. for one day, the reaction mixture was washed with water. The organic layer was dried over magnesium sulfate and concentrated to a viscous oil. The product crystallized from isopropyl ether solution to afford 2.0 g of a white solid. Trace amounts of impurities were removed by passing through a silica gel column. m.p. 136°-138° C.

Calc'd for $C_{23}H_{31}N_3O_5S_2$: C, 55.96; H, 6.33; N, 8.51; Found: C, 55.83; H, 6.25; N, 8.45

EXAMPLE 5

Preparation of [N-Methyl-N-[N'-methyl-N'-[1-(2-(2'-methylphenyl)-5,5-dimethyl-3-oxo-1-cyclohexenyl)oxycarbonyl]aminosulfenyl]carbamoyloximino]-2-methyl-2-methylsulfonyl propionaldehyde. (Method III)

To a solution of 2.93 g (0.0074 m) of 1-[N-methyl-N-[N'-methyl-N'-fluorocarbonylaminosulfenyl] carbamoyloxy] 2-(2'-methylphenyl) 5,5-dimethyl-1-cyclohexen-3-one (prepared as in Example 1) and 1.22 g (0.0074 m) of 2-methyl-2-methylsulfonylpropionaldoxime in 40 ml of toluene and 10 ml of methylene chloride was added 0.75 g (0.0074 m) of triethylamine. After stirring for 72 hours at room temperature the reaction mixture was washed successively with 5 percent sodium carbonate and water until the wash was neutral. The organic layer was dried and concentrated to a residual solid. The crude solid was purified by dry column silica gel chromatography to afford 2.2 g of a white solid. m.p. 143°-144° C.

Calc'd for: $C_{24}H_{23}N_3O_7S_2$: C, 53.42; H, 6.16; N, 7.78; Found: C, 53.09; H, 6.08; N, 7.70

EXAMPLE 7

Preparation of N,N'-bis-[1-[N-methylcarbamoyloxy]-2-(2'-methylphenyl)-5,5-dimethyl-1-cyclohexen-3-one] sulfide. (Method I)

To a solution of 9.2 g (0.04 m) of 2-(2'-methylphenyl)-5,5 dimethylcyclohexan-1,3-dione in toluene with a little of methylene chloride was added 3.04 g (0.02 m) of bis-(N-methyl-N-fluorocarbonylamino) sulfide followed by dropwise addition of 4.05 g (0.04 m) of triethylamine. After stirring at room temperature for three days the reaction mixture was washed successively with 2 percent sodium carbonate solution and water. The organic layer was dried and concentrated to afford 9.46 g of a light yellow semisolid. Chromatographic purification using silica gel afforded 5.08 g of a white solid. m.p. 84°-88° C.

Calc'd for $C_{34}H_{40}N_2O_6S$: C, 67.52; H, 6.67; N, 4.63; Found: C, 67.29; H, 6.72; N, 7.48

The following Examples 4, 6, 8-24 were conducted by either of Methods I or III utilizing the specific procedures outlined in Examples 3, 5 and 7. The resultant compounds and physical data are indicated in Table I.

TABLE I

| Ex. No. | COMPOUND | MP °C. | Mol. Formula | Calculated C | Calculated H | Calculated N | Found C | Found H | Found N |
|---|---|---|---|---|---|---|---|---|---|
| 4 | (structure) | 134–139 | $C_{22}H_{29}N_3O_5S_2$ | 55.09 | 6.09 | 8.76 | 54.54 | 6.13 | 8.88 |
| 6 | (structure) | oil | $C_{25}H_{35}N_3O_7S_2$ | (Structure confirmed by NMR and IR spectral data) | | | | | |
| 8 | (structure) | oil | $C_{36}H_{44}N_2O_6S$ | 68.33 | 7.01 | 4.42 | 67.15 | 6.83 | 4.77 |
| 9 | (structure) | 174–177 | $C_{34}H_{40}N_2O_6S_2$ | 64.12 | 6.33 | 4.40 | 64.10 | 6.24 | 4.47 |
| 10 | (structure) | 116–118 | $C_{26}H_{30}N_2O_5S_2$ | 60.68 | 5.87 | 5.44 | 61.02 | 5.88 | 5.41 |

TABLE I-continued

| Ex. No. | COMPOUND | MP °C. | Mol. Formula | Calculated C | H | N | Found C | H | N |
|---|---|---|---|---|---|---|---|---|---|
| 11 | (structure) | amorphous solid | $C_{27}H_{32}N_2O_5S_2$ | 61.34 | 6.10 | 5.30 | 60.72 | 6.04 | 5.28 |
| 12 | (structure) | oil | $C_{28}H_{34}N_2O_5S_2$ | 61.97 | 6.31 | 5.16 | 61.40 | 6.22 | 5.13 |
| 13 | (structure) | oil | $C_{28}H_{34}N_2O_5S$ | 65.86 | 6.71 | 5.48 | 65.18 | 6.57 | 5.35 |
| 14 | (structure) | oil | $C_{28}H_{34}N_2O_6S$ | 63.85 | 6.51 | 5.32 | 63.38 | 6.30 | 5.39 |
| 15 | (structure) | amorphous solid | $C_{29}H_{34}N_2O_5S_3$ | 59.36 | 5.84 | 4.77 | 59.14 | 5.67 | 4.74 |
| 16 | (structure) | amorphous solid | $C_{30}H_{36}N_2O_5S$ | 67.14 | 6.76 | 5.22 | 65.98 | 6.84 | 5.64 |
| 17 | (structure) | 132–134 | $C_{29}H_{30}N_2O_5S$ | 67.16 | 5.83 | 5.40 | 67.01 | 5.73 | 5.43 |
| 18 | (structure) | 124.5–126.5 | $C_{30}H_{32}N_2O_5S$ | 67.64 | 6.06 | 5.26 | 67.25 | 5.88 | 5.26 |
| 19 | (structure) | oil | $C_{29}H_{34}N_2O_6S_2$ | 61.03 | 6.00 | 4.91 | 60.30 | 5.84 | 4.82 |

TABLE I-continued

| Ex. No. | COMPOUND | MP °C. | Mol. Formula | Elemental Analyses Calculated C | H | N | Found C | H | N |
|---|---|---|---|---|---|---|---|---|---|
| 20 | (structure with O-C-N-S-N-C-O linkage, CH3 groups, benzofuran with two CH3) | amorphous solid | $C_{30}H_{36}N_2O_6S$ | 65.19 | 6.57 | 5.07 | 64.33 | 6.41 | 5.18 |
| 21 | (structure with O-C-N-S-N-C-O linkage, CH3 groups, benzodioxole with two CH3) | amorphous solid | $C_{29}H_{34}N_2O_7S$ | 62.80 | 6.18 | 5.05 | 62.06 | 6.05 | 5.09 |
| 22 | (structure with O-C-N-S-N-C-O-N=N linkage, thiazolidinone with CH3 groups) | 146–148 | $C_{26}H_{34}N_4O_6S_2$ | 55.79 | 6.09 | 9.96 | 55.21 | 5.98 | 9.84 |
| 23 | (structure with O-C-N-S-N-C-O-N linkage, dithiane) | 108–110 | $C_{24}H_{31}N_3O_5S_3$ | 53.61 | 5.81 | 7.81 | 53.06 | 5.67 | 7.73 |
| 24 | (structure with O-C-N-S-N-C-O-N=C-CH3, SCH3) | amorphous solid | $C_{24}H_{33}N_3O_5S_2$ | 56.78 | 6.55 | 8.28 | 56.64 | 6.61 | 8.23 |

Selected species of the new compounds were evaluated to determine their pesticidal activity against mites, nematodes, and certain insects, including an aphid, a caterpillar, a beetle and a fly.

Suspensions of the test compounds were prepared by dissolving one gram of compound in 50 milliliters of acetone in which had been dissolved 0.1 gram (10 percent of the weight of compound) of an alkylphenoxy polyethoxyethanol surfactant, as an emulsifying or dispersing agent. The resulting solution was mixed into 150 milliliters of water to give roughly 200 milliliters of a suspension containing the compound in finely divided form. The thus-prepared stock suspension contained 0.5 percent by weight of compound. The concentrations in parts per million by weight employed in the tests described below were obtained by appropriate dilutions of the stock suspension with water. The test procedures were as follows:

Adults and nymphal stages of the bean aphid (*Aphis fabae* Scop.) reared on potted dwarf nasturtium plants at 65°–70° F. and 50±5 percent relative humidity, constituted with test insects. For testing purposes, the number of aphids per pot was standardized to 100–150 by trimming plants containing excess aphids.

The test compounds were formulated by diluting the stock suspension with water to give a suspension containing 500 parts of test compound per million parts of final formulation.

The potted plants (one pot per compound tested) infested with 100–150 aphids, were placed on a revolving turntable and sprayed with 100–110 milliliters of test comound formulation by use of a DeVilbiss spray gun set at 40 psig. air pressure. This application, which lasted 25 seconds, was sufficient to wet the plants to run-off. As a control, 100–110 milliliters of a water-acetone-emulsifier solution containing no test compound were also sprayed on infested plants. After spraying, the pots were placed on their sides on a sheet of white standard mimeograph paper which had been previously ruled to facilitate counting. Temperature and humidity in the test room during the 24 hour holding period were 65°–70° F. and 50–70 percent, respectively. Aphids which fell onto the paper and were unable to remain standing after being uprighted were considered dead. Aphids remaining on the plants were observed closely for movement and those which were unable to move the length of the body upon stimulation by prodding were considered dead.

Larvae of the southern armyworm (*Spodopteraeridania*, (Cram.)), reared on Tendergreen bean plants at a temperature of 80°±5° F. and a relative humidity of 50±5 percent, constituted the test insects.

The test compounds were formulated by diluting the stock suspension with water to give a suspension containing 500 parts of test compound per million parts of final formulation. Potted Tendergreen bean plants of standard height and age were placed on a revolving turntable and sprayed with 100–110 milliliters of test compound formulation by use of a DeVilbiss spray gun set at 10 psig air pressure. This application, which lasted 25 seconds, was sufficient to wet plants to run-off. As a control, 100–110 milliliters of a water-acetone-emulsifier solution containing no test compound were also sprayed on infested plants. When dry, the paired leaves were separated and each one was placed in a 9 centimeter Petri dish lined with moistened filter paper. Five randomly selected larvae were introduced into each dish and the dishes were closed. The closed dishes were labeled and held at 80°–85° F. for three days. Although the larvae could easily consume the whole leaf within twenty-four hours, no more food was added. Larvae which were unable to move the length of the body, even upon stimulation by prodding, were considered dead.

Fourth instar larvae of the Mexican bean beetle (*Epilachna varivestis*, Muls.), reared on Tendergreen bean plants at a temperature of 80°±5° F. and 50±5 percent relative humidity, were the test insects.

The test compounds were formulated by diluting the stock suspension with water to give a suspension containing 500 parts of test compound per million parts of final formulation. Potted Tendergreen bean plants of standard height and age were placed on a revolving turntable and sprayed with 100–110 milliliters of test compound formulation by use of a DeVilbiss spray gun set at 10 psig air pressure. This application, which lasted 25 seconds, was sufficient to wet plants to run-off. As a control, 100–110 milliliters of a water-acetone-emulsifier solution containing no test compound were also sprayed on infested plants. When dry, the paired leaves were separated and each was placed in a 9 centimeter Petri dish lined with moistened filter paper. Five randomly selected larvae were introduced into each dish, and the dishes were closed. The closed dishes were labeled and held at a temperature of 80°±5° F. for three days. Although the larvae could easily consume the leaf within 24 to 48 hours, no more food was added. Larvae which were unable to move the length of the body, even upon stimulation, were considered dead.

Four to six day old adult house flies (*Musca domestica*, L.), reared according to the specifications of the Chemical Specialties Manufacturing Association (Blue Book, McNair-Dorland Co., N.Y. 1954; pages 243–244, 261) under controlled conditions of 80°±5° F. and 50±5 percent relative humidity, were the test insects. The flies were immobilized by anesthetizing with carbon dioxide and twenty five immobilized individuals, males and females, were transferred to a cage consisting of a standard food strainer about five inches in diameter which was inverted over a wrapping-paper-covered surface. The test compounds were formulated by diluting the stock suspension with a 10 percent (by weight) sugar solution to give a suspension containing 500 parts of test compound per million parts of final formulation, by weight. Ten milliliters of the test formulation were added to a souffle cup containing a one-inch square of an absorbent cotton pad. This bait cup was introduced and centered on the blotting paper under the food strainer prior to admitting the anesthetized flies. The caged flies were allowed to feed on the bait for twenty four hours, at a temperature of 80°±5° F. and the relative humidity of 50±5 percent. Flies which showed no sign of movement on prodding were considered dead.

Adults and nymphal stages of the two-spotted mite (*Tetranychus urticae* Koch), reared on Tendergreen bean plants at 80±5 percent relative humidity, were the test organisms. Infested leaves from a stock culture were placed on the primary leaves of two bean plants six to eight inches in height, growing in a two-and-a-half inch clay pot. 150–200 Mites, a sufficient number for testing, transferred from the excised leaves to the fresh plants in a period of twenty-four hours. Following the twenty-four hour transfer period, the excised leaves were removed from the infested plants. The test compounds were formulated by diluting the stock suspension with water to give a suspension containing 500 parts of test compound per million parts of final formulation. The potted plants (one pot per compound) were placed on a revolving turntable and sprayed with 100–110 milliliters of test compound formulation by use of a DeVilbiss spray gun set at 40 psig. air pressure. This application, which lasted 25 seconds, was sufficient to wet the plants to run-off. As a control, 100–110 milliliters of water solution containing acetone and emulsifier in the same concentration as the test compound formulation, but containing no test compound, were also sprayed on infested plants. The sprayed plants were held at 80±5 percent relative humidity for six days, after which a mortality count of motile forms was made. Microscopic examination for motile forms was made on the leaves of the test plants. Any individual which was capable of locomotion upon prodding was considered living.

The results of these tests are set forth in Table I below. In these tests the pesticidal activity of the compounds at the indicated dosage rate against aphid, mite, Southern Armyworm, Bean Beetle and house fly was rated as follows:
A = excellent control
B = partial control
C = no control
Dashes indicate no test conducted.

BIOLOGICAL ACTIVITY

| Ex. No. | STRUCTURE | Bean Aphid | 2-Spotted Mite | 2-SM (Egg) | Southern Armyworm | Mexican Bean Beetle | House Fly |
|---|---|---|---|---|---|---|---|
| 1 | 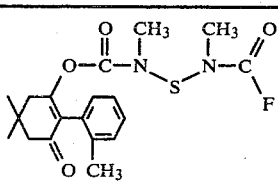 | B | A | A | C | C | C |

-continued

BIOLOGICAL ACTIVITY

| Ex. No. | STRUCTURE | Bean Aphid | 2-Spotted Mite | 2-SM (Egg) | Southern Armyworm | Mexican Bean Beetle | House Fly |
|---|---|---|---|---|---|---|---|
| 2 | 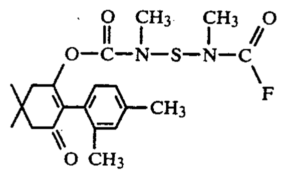 | C | A | A | C | C | C |
| 3 | 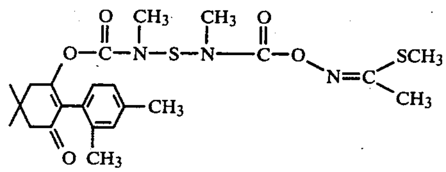 | A | B | — | A | A | A |
| 4 | 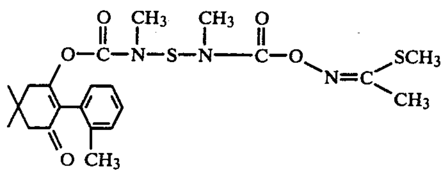 | A | C | — | A | A | A |
| 5 | 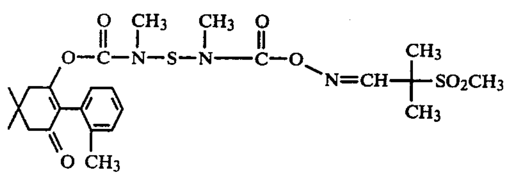 | C | A | — | C | C | C |
| 6 | 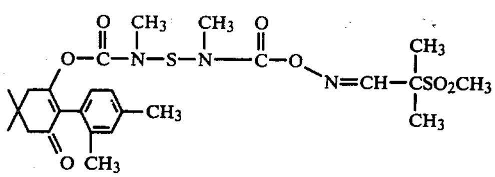 | C | A | A | C | A | C |
| 7 | 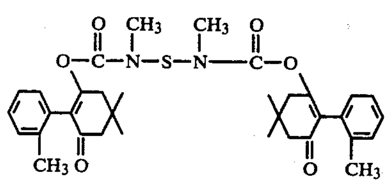 | C | B | A | C | C | C |
| 8 | 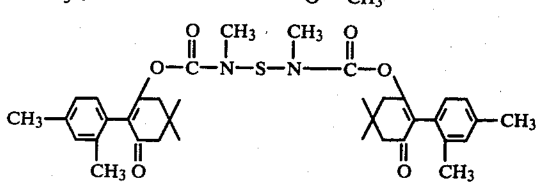 | C | A | A | C | C | C |
| 9 | 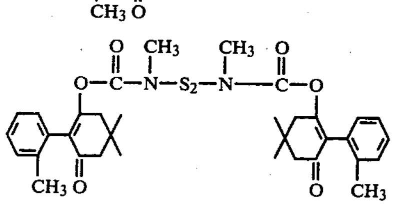 | C | B | A | C | C | C |
| 10 | 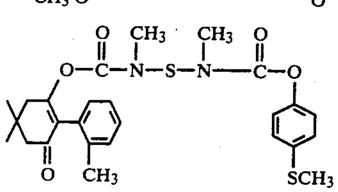 | C | C | A | C | C | A |

-continued

BIOLOGICAL ACTIVITY

| Ex. No. | STRUCTURE | Bean Aphid | 2-Spotted Mite | 2-SM (Egg) | Southern Armyworm | Mexican Bean Beetle | House Fly |
|---|---|---|---|---|---|---|---|
| 11 | 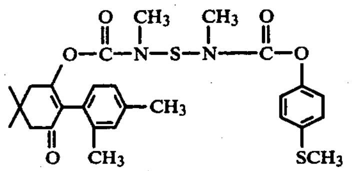 | C | C | A | C | B | A |
| 12 | 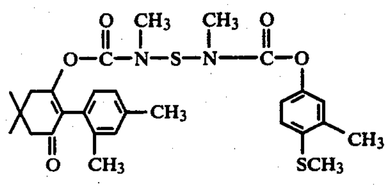 | C | C | A | A | A | A |
| 13 | 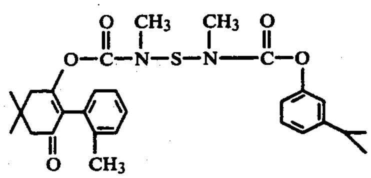 | C | C | A | B | A | B |
| 14 | 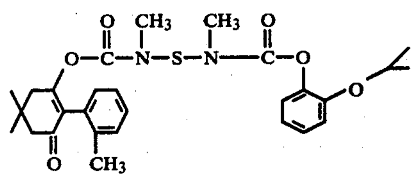 | C | B | A | C | A | A |
| 15 | 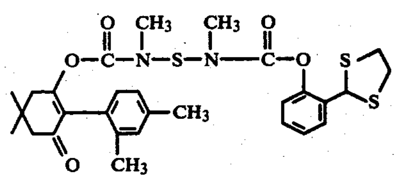 | C | A | A | B | A | A |
| 16 | 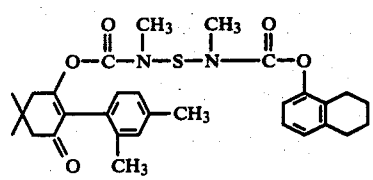 | C | A | A | B | A | C |
| 17 | 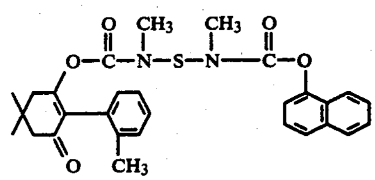 | C | B | A | A | A | C |
| 18 | 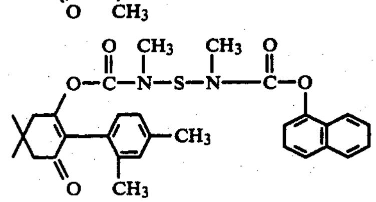 | C | B | A | A | A | C |
| 19 | 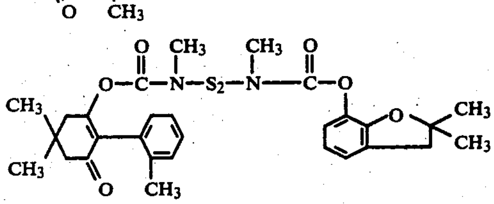 | A | C | A | A | A | A |

-continued

| Ex. No. | STRUCTURE | Bean Aphid | 2-Spotted Mite | 2-SM (Egg) | Southern Armyworm | Mexican Bean Beetle | House Fly |
|---|---|---|---|---|---|---|---|
| 20 | 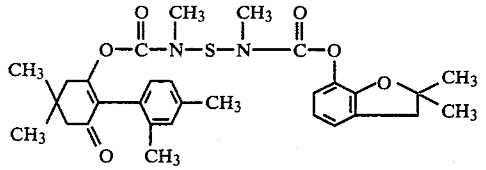 | A | B | A | A | A | A |
| 21 | 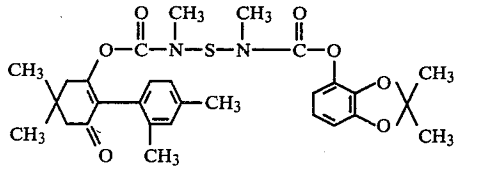 | B | A | A | A | A | A |
| 22 | 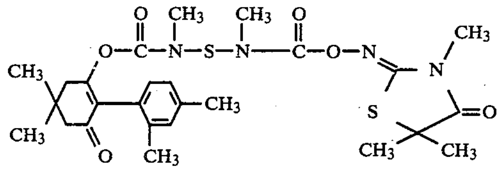 | C | A | A | C | C | C |
| 23 | 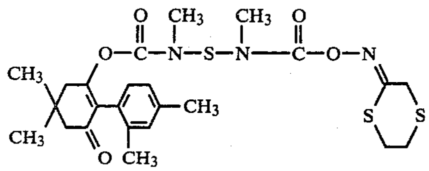 | B | A | A | A | A | A |
| 24 | 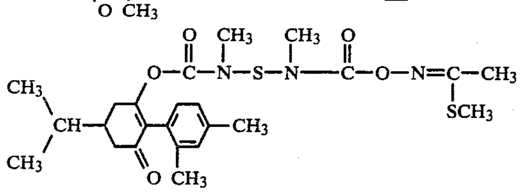 | A | A | A | A | A | A |

BIOLOGICAL ACTIVITY

It will be understood that the plant species employed in the above tests are merely representative of a wide variety of plant pest that can be controlled by the use of the compounds of this invention. The compounds contemplated in this invention may be applied as mite ovicides and miticides according to methods known to those skilled in the art. Pesticidal compositions containing the compounds as the active toxicant will usually comprise a carrier and/or diluent, either liquid or solid.

Suitable liquid diluents or carriers include water, petroleum distillates, or other liquid carriers with or without surface active agents. Liquid concentrates may be prepared by dissolving one of these compounds with a nonphytotoxic solvent such as acetone, xylene, or nitrobenzene and dispersing the toxicants in water with the aid of suitable surface active emulsifying and dispersing agents.

The choice of dispersing and emulsifying agents and the amount employed in dictated by the nature of the composition and the ability of the agent to facilitate the dispersion of the toxicant. Generally, it is desirable to use as little of the agent as is possible, consistent with the desired dispersion of the toxicant in the spray so that rain does not reemulsify the toxicant after it is applied to the plant and wash it off the plant. Nonionic, anionic, amphoteric or cationic dispersing and emulsifying agents may be employed; for example, the condensation products of alkylene oxides with phenol and organic acids, alkyl aryl sulfonates, complex ether alcohols, quaternary ammonium compounds, and the like.

In the preparation of wettable powder or dust or granulated compositions, the active ingredient is dispersed in and on an appropriately divided solid carrier such as clay, talc, bentonite, diatomaceous earth, fullers earth, and the like. In the formulation of the wettable powders the aforementioned dispersing agents as well as lignosulfonates can be included.

The required amount of the toxicants contemplated herein may be applied per acre treated in from 1 to 200 gallons or more of liquid carrier and/or diluent or in from about 5 to 500 pounds of inert solid carrier and/or diluent. The concentration in the liquid concentrate will usually vary from about 10 to 95 percent by weight and in the solid formulations from about 0.5 to about 90 percent by weight. Satisfactory sprays, dusts, or granules for general use contain from about ¼ to 15 pounds of active toxicant per acre.

The pesticides contemplated herein prevent attack by insects and mites upon plants or other material to which the pesticides are applied, and they have relatively high residual toxicity. With respect to plants, they have a high margin of safety in that when used in sufficient amount to kill or repel the insects, they do not burn or injure the plant, and they resist weathering which includes wash-off caused by rain, decomposition by ultraviolet light, oxidation, or hydrolysis in the presence of moisture or, at least such decomposition, oxidation, and hydrolysis as would materially decrease the desirable pesticidal characteristic of the toxicants or impart undesirable characteristic for instance, phytotoxicity, to the toxicants. The toxicants are so chemically inert that they are compatible with substantially any other constituents of the spray schedule, and they may be used in the soil, upon the seeds, or the roots of plants without injuring either the seeds or roots of plants. They may also be used in combination with other pesticidally active compounds. When used as miticides they will normally be applied to the foliage of the plants to be treated. It will be appreciated that the compounds of this invention can also be used in combination with other biologically active compounds.

What is claimed is:

1. Compounds of the formula:

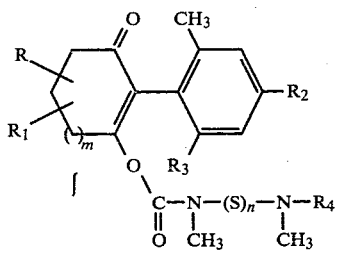

wherein:
m=0 or 1;
n=1 or 2;
R, R₁, R₂, and R₃ are individually hydrogen or alkyl groups of one to four carbon atoms;
R₄ is:
(a) fluorocarbonyl or
(b) a group of the formula:

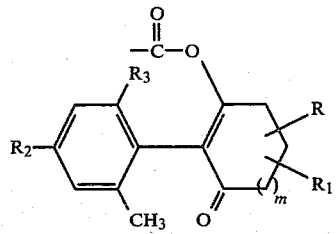   A.

wherein R, R₁, R₂, R₃ and m have the above indicated values;

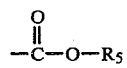   B.

wherein R₅ is:
(1) a phenyl group which is unsubstituted or substituted with one or more C₁-C₁₂ alkyl, chloro, fluoro, bromo, alkoxy, alkylthio, alkylthioalkyl, alkylsulfinyl, alkylsulfinylalkyl, alkylsulfonyl, alkylsulfonylalkyl, alkynyloxy, dialkylamino, alkoxyamino, formamidino, cyano, dioxolanyl or dithiolanyl group in any combination; or
(2) a naphthyl, tetrahydronaphthyl, dihydrobenzofuranyl, benzodioxalanyl, or benzothienyl group, all of which is unsubstituted or substituted with one or more alkyl groups; or
(3) a group of the formula:

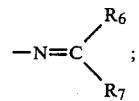

wherein R₆ is a chloro, alkyl, alkylthio, cyanoalkylthio, amidoalkylthio or cyano group; or R₆ is hydrogen provided R₇ is not hydrogen;
R₇ is an alkyl, alkylthio, alkoxycarbonyl, aminocarbonyl, alkylaminocarbonyl, dialkylaminocarbonyl, alkylthioalkyl, cyanoalkyl, alkylsulfinylalkyl, alkylsulfonylalkyl, alkoxyalkyl, nitroalkyl, hydroxyalkyl, or phenyl group, said phenyl group is unsubstituted or substituted with one or more alkyl, chloro, or fluoro groups in any combination; or R₇ is hydrogen, provided R₆ is not hydrogen; or
(4) cyclic oximes selected from the group consisting of 2-oximino-1,4-dithianes, 2-oximino-1,3-dithianes, 4-oximino-1,3-dithiolanes, 2-oximino-1,4-dioxanes, 2-oximino-tetrahydro-1,4-thiazine-3-ones, 2-oximino-1,3-dihiolanes, 2-imino-4-oximino-1,3-dithiolanes, 3-oximinothiophanes, 2-oximinothiophanes, 2-oximino-tetrahydro-1,4-oxazine-3-ones, 2-oximino-1,4-oxathianes, 4-oximino-1,3-oxathiolanes, 2-oximino-thiazolidin-3-ones, 2-oximino-1,3-thiazolidin-4-ones or 2-oximino-tetrahydro-1,4-thiazin-5-ones, each of which is unsubstituted or substituted with one to four alkyl groups and wherein sulfur can be in any of its oxidation states.

2. A compound according to claim 1 wherein R, R₁, R₂ and R₃ are individually hydrogen, methyl and isopropyl.

3. A compound according to claim 1 wherein R₆ is hydrogen, lower alkyl and alkylthio.

4. A compound according to claim 1 wherein R₇ is lower alkyl, alkylthioalkyl, cyanoalkyl and alkylsulfonylalkyl.

5. Compounds of the formula:

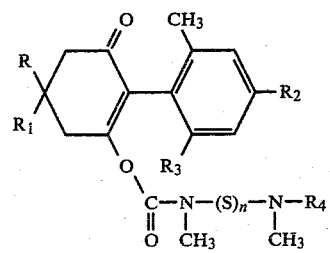

wherein:
n=1 or 2;
R, R₁ and R₂ are individually hydrogen or alkyl groups of one to four carbon atoms;
R₃ is hydrogen;
R₄ is:
(a) fluorocarbonyl or
(b) a group of the formula:

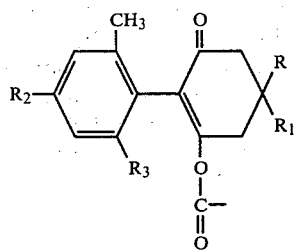 A.

wherein R, R₁, R₂, and R₃ have the above indicated values;

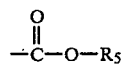 B.

wherein $R_5$ is:
(1) a phenyl group which is unsubstituted or substituted with one or more $C_1$-$C_{12}$ alkyl, chloro, fluoro, bromo, alkoxy, alkylthio, alkylthioalkyl, alkylsulfinyl, alkylsulfinylalkyl, alkylsulfonyl, alkylsulfonylalkyl, alkynyloxy, dialkylamino, alkoxyamino, formamidino, cyano, dioxolanyl or dithiolanyl group in any combination; or
(2) a naphthyl, tetrahydronaphthyl, dihydrobenzofuranyl, benzodioxolanyl, or benzothienyl group, all of which is unsubstituted or substituted with one or more alkyl groups; or
(3) a group of the formula:

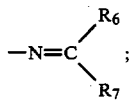

wherein $R_6$ is a chloro, alkyl, alkylthio, cyanoalkylthio, amidoalkylthio or cyano group; or $R_6$ is hydrogen provided $R_7$ is not hydrogen;
$R_7$ is an alkyl, alkylthio, alkoxycarbonyl, aminocarbonyl, alkylaminocarbonyl, dialkylaminocarbonyl, alkylthioalkyl, cyanoalkyl, alkylsulfinylalkyl, alkylsulfonylalkyl, alkoxyalkyl, nitroalkyl, hydroxyalkyl, or phenyl group, said phenyl group is unsubstituted or substituted with one or more alkyl, chloro, or fluoro groups in any combination; or $R_7$ is hydrogen, provided $R_6$ is not hydrogen; or
(4) cyclic oximes selected from the group consisting of 2-oximino-1,4-dithianes, 2-oximino-1,3-dithianes, 4-oximino-1,3-dithiolanes, 2-oximino-1,4-dioxanes, 2-oximino-tetrahydro-1,4-thiazine-3-ones, 2-oximino-1,3-dithiolanes, 2-imino-4-oximino-1,3-dithiolanes, 3-oximinothiophanes, 2-oximinothiophanes, 2-oximinotetrahydro-1,4-oxazine-3-ones, 2-oximino-1,4-oxathianes, 4-oximino-1,3-oxathiolanes, 2-oximino-thiazolidin-3-ones, 2-oximino-1,3-thiazolidin-4-ones or 2-oximino-tetrahydro-1,4-thiazin-5-ones, each of which is unsubstituted or substituted with one to four groups and wherein sulfur can be in any of its oxidation states.

6. A compound according to claim 5 wherein R, R₁ and R₂ are individually hydrogen, methyl and isopropyl.

7. A compound according to claim 5 wherein R₆ is hydrogen, lower alkyl and alkylthio.

8. A compound according to claim 5 wherein R₇ is lower alkyl, alkylthioalkyl, cyanoalkyl and alkylsulfonylalkyl.

9. A compound according to claim 5 wherein R, R₁ and R₂ are individually hydrogen, methyl and isopropyl;
R₆ is hydrogen, lower alkyl and alkylthio;
R₇ is lower alkyl, alkylthioalkyl, cyanoalkyl and alkylsulfonylalkyl.

10. 1-[N-Methyl-N-[N'-methyl-N'-fluorocarbonylaminosulfenyl] carbamoyloxy]-2-(2'-methylphenyl)-5,5-dimethyl-1-cyclohexene-3-one.

11. 1-[N-Methyl-N-[N'-methyl-N'-fluorocarbonylaminosulfenyl]carbamoyloxy]-2-(2',4'-dimethylphenyl)-5,5-dimethyl-1-cyclohexene-3-one.

12. S-Methyl-N-[N'-[N''-methyl-N''-[1-(2-(2',4'-dimethylphenyl)-5,5-dimethyl-1-cyclohexenyl-3-one) oxycarbonyl]aminosulfenyl]-N'-methylcarbamoyloxy] acetimidate.

13. 1-[N-methyl-N-[N'-methyl-N'-[1-(2-(2'-methylphenyl)-5,5-dimethyl-3-oxo-1-cyclohexenyl) oxycarbonyl] aminosulfenyl] carbamoyloxy] naphthalene.

14. 7-[N-methyl-N-[N'-methyl-N'-[1-(2-(2',4'-dimethylphenyl)-5,5-dimethyl-3-oxo-1-cyclohexenyl) oxycarbonyl] aminosulfenyl] carbamoyloxy]-2,2-dimethyl-2,3-dihydrobenzofuran.

15. 4-[N-methyl-N-[N'-methyl-N'-[1-(2-(2',4'-dimethylphenyl)-5,5-dimethyl-3-oxo-1-cyclohexenyl) oxycarbonyl] aminosulfenyl] carbamoyloxy]-2,2-dimethylbenzodioxolan.

16. S-Methyl-N-[N'-[N''-methyl-N''-[1-(2-(2',4'-dimethylphenyl)-5-isopropyl-1-cyclohexene-3-one) oxycarbonyl]aminosulfenyl]-N'-methylcarbamoyloxy] acetimidate.

17. An insecticidal and acaricidal composition comprising an acceptable carrier and as the active toxicant an insecticidally and acaricidally effective amount of a compound of the formula:

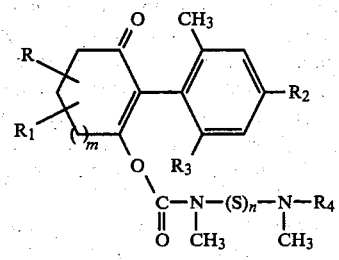

wherein:
m=0 or 1;
n=1 or 2;
R, R₁, R₂, and R₃ are individually hydrogen or alkyl groups of one to four carbon atoms;
R₄ is:
(a) fluorocarbonyl or
(b) a group of the formula:

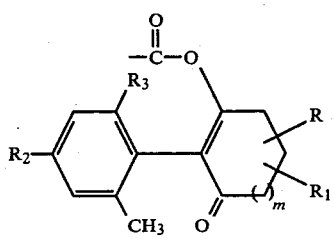

A.

wherein R, R$_1$, R$_2$, R$_3$ and m have the above indicated values;

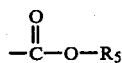

B.

wherein R$_5$ is:
(1) a phenyl group which is unsubstituted or substituted with one or more C$_1$-C$_{12}$ alkyl, chloro, fluoro, bromo, alkoxy, alkylthio, alkylthioalkyl, alkylsulfinyl, alkylsulfinylalkyl, alkylsulfonyl, alkylsulfonylalkyl, alkynyloxy, dialkylamino, alkoxyamino, formamidino, cyano, dioxolanyl or dithiolanyl group in any combination; or
(2) a naphthyl, tetrahydronaphthyl, dihydrobenzofuranyl, benzodioxalanyl, or benzothienyl group, all of which is unsubstituted or substituted with one or more alkyl groups; or
(3) a group of the formula:

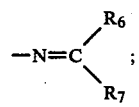

wherein R$_6$ is a chloro, alkyl, alkylthio, cyanoalkylthio, amidoalkylthio or cyano group; or R$_6$ is hydrogen provided R$_7$ is not hydrogen;
R$_7$ is an alkyl, alkylthio, alkoxycarbonyl, aminocarbonyl, alkylaminocarbonyl, dialkylaminocarbonyl, alkylthioalkyl, cyanoalkyl, alkylsulfinylalkyl, alkylsulfonylalkyl, alkoxyalkyl, nitroalkyl, hydroxyalkyl, or phenyl group, said phenyl group is unsubstituted or substituted with one or more alkyl, chloro, or fluoro groups in any combination; or R$_7$ is hydrogen, provided R$_6$ is not hydrogen; or
(4) cyclic oximes selected from the group consisting of 2-oximino-1,4-dithianes, 2-oximino-1,3-dithianes, 4-oximino-1,3-dithiolanes, 2-oximino-1,4-dioxanes, 2-oximino-tetrahydro-1,4-thiazine-3-ones, 2-oximino-1,3-dithiolanes, 2-imino-4-oximino-1,3-dithiolanes, 3-oximinothiophanes, 2-oximinothiophanes, 2-oximinotetrahydro-1,4-oxazine-3-ones, 2-oximino-1,4-oxathianes, 4-oximino-1,3-oxathiolanes, 2-oximino-thiazolidin-3-ones, 2-oximino-1,3-thiazolidin-4-ones or 2-oximino-tetrahydro-1,4-thiazin-5-ones, each of which is unsubstituted or substituted with one to four alkyl groups and wherein sulfur can be in any of its oxidation states.

18. A composition according to claim 17 wherein R, R$_1$, R$_2$ and R$_3$ are individually hydrogen, methyl and isopropyl.

19. A composition according to claim 17 wherein R$_6$ is hydrogen, lower alkyl and alkylthio.

20. A composition according to claim 17 wherein R$_7$ is lower alkyl, alkylthioalkyl, cyanoalkyl and alkylsulfonylalkyl.

21. An insecticidal and acaricidal composition comprising an acceptable carrier and as the active toxicant an insecticidally and acaricidally effective amount of a compound of the formula:

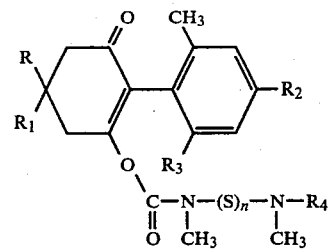

wherein:
n=1 or 2;
R, R$_1$ and R$_2$ are individually hydrogen or alkyl groups of one to four carbon atoms;
R$_3$ is hydrogen;
R$_4$ is:
(a) fluorocarbonyl or
(b) a group of the formula:

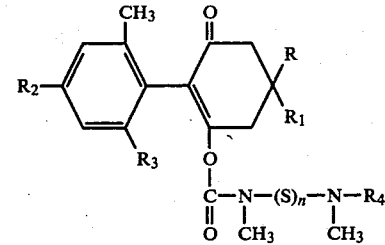

A.

wherein R, R$_1$, R$_2$, and R$_3$ have the above indicated values:

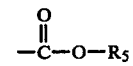

B.

wherein R$_5$ is:
(1) a phenyl group which is unsubstituted or substituted with one or more C$_1$-C$_{12}$ alkyl, chloro, fluoro, bromo, alkoxy, alkylthio, alkylthioalkyl, alkylsulfinyl, alkylsulfinylalkyl, alkylsulfonyl, alkylsulfonylalkyl, alkynyloxy, dialkylamino, alkoxyamino, formamidino, cyano, dioxolanyl or dithiolanyl group in any combination; or
(2) a naphthyl, tetrahydronaphthyl, dihydrobenzofuranyl, benzodioxalanyl, or benzothienyl group, all of which is unsubstituted or substituted with one or more alkyl groups; or
(3) a group of the formula:

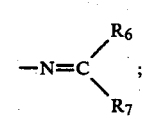

wherein R$_6$ is a chloro, alkyl, alkylthio, cyanoalkylthio, amidoalkylthio or cyano group; or R$_6$ is hydrogen provided R$_7$ is not hydrogen;

R7 is an alkyl, alkylthio, alkoxycarbonyl, aminocarbonyl, alkylaminocarbonyl, dialkylaminocarbonyl, alkylthioalkyl, cyanoalkyl, alkylsulfinylalkyl, alkylsulfonylalkyl, alkoxyalkyl, nitroalkyl, hydroxyalkyl, or phenyl group, said phenyl group is unsubstituted or substituted with one or more alkyl, chloro, or fluoro groups in any combination; or R7 is hydrogen, provided R6 is not hydrogen; or (4) cyclic oximes selected from the group consisting of 2-oximino-1,4-dithianes, 2-oximino-1,3-dithianes, 4-oximino-1,3-dithiolanes, 2-oximino-1,4-dioxanes, 2-oximino-tetrahydro-1,4-thiazine-3-ones, 2-oximino-1,3-dithiolanes, 2-imino-4-oximino-1,3-dithiolanes, 3-oximinothiophanes, 2-oximinothiophanes, 2-oximinotetrahydro-1,4-oxazine-3-ones, 2-oximino-1,4-oxathianes, 4-oximino-1,3-oxathiolanes, 2-oximino-thiazolidin-3-ones, 2-oximino-1,3-thiazolidin-4-ones or 2-oximino-tetrahydro-1,4-thiazin-5-ones, each of which is unsubstituted or substituted with one to four alkyl groups and wherein sulfur can be in any of its oxidation states.

22. A composition according to claim 21 wherein R, R1 and R2 are individually hydrogen, methyl and isopropyl.

23. A composition according to claim 21 wherein R6 is hydrogen, lower alkyl and alkylthio.

24. A composition according to claim 21 wherein R7 is lower alkyl, alkylthioalkyl, cyanoalkyl and alkylsulfonylalkyl.

25. A composition according to claim 21 wherein R, R1 and R2 are individually hydrogen, methyl and isopropyl;
R6 is hydrogen, lower alkyl and alkylthio;
R7 is lower alkyl, alkylthioalkyl, cyanoalkyl and alkylsulfonylalkyl.

26. A composition according to claim 21 wherein the active toxicant is 1-[N-Methyl-N-[N'-methyl-N'-methyl-N'-fluorocarbonylaminosulfenyl]carbamoyloxy]-2-(2'-methylphenyl)-5,5-dimethyl-1-cyclohexene-3-one.

27. A composition according to claim 21 wherein the active toxicant is 1-[N-Methyl-N-[N'-methyl-N'-fluorocarbonylaminosulfenyl]carbamoyloxy]-2-(2',4'-dimethylphenyl)-5,5-dimethyl-1-cyclohexene-3-one.

28. A composition according to claim 21 wherein the active toxicant is S-Methyl-N-[N'-[N''-methyl-N''-[1-(2-(2',4'-dimethylphenyl)-5,5-dimethyl-1-cyclohexene-3-one)oxycarbonyl]aminosulfenyl]-N'-methylcarbamoyloxy]acetimidate.

29. A composition according to claim 21 wherein the active toxicant is 1-[N-methyl-N-[N'-methyl-N'-[1-(2-(2'-methylphenyl)-5,5-dimethyl-3-oxo-1-cyclohexenyl)oxycarbonyl]aminosulfenyl]carbamoyloxy]naphthalene.

30. A composition according to claim 21 wherein the active toxicant is 7-[N-methyl-N-[N'-methyl-N'-[1-(2-(2',4'-dimethylphenyl)-5,5-dimethyl-3-oxo-1-cyclohexenyl)oxycarbonyl]aminosulfenyl]carbamoyloxy]-2,2-dimethyl-2,3-dihydrobenzofuran.

31. A composition according to claim 21 wherein the active toxicant is 4-[N-methyl-N-[N'-methyl-N'-[1-(2-(2',4'-dimethylphenyl-5,5-dimethyl-3-oxo-1-cyclohexenyl)oxycarbonyl]aminosulfenyl]-2,2-dimethylbenzodioxolan.

32. A composition according to claim 21 wherein the active toxicant is S-Methyl-N-[N'-[N''-methyl-N''-[1-(2-(2',4'-dimethylphenyl)-5-isopropyl-1-cyclohexene-3-one) oxycarbonyl]aminosulfenyl]-N'-methylcarbamoyloxy]acetimidate.

33. A method of controlling insects and acarids which comprises subjecting them to an insecticidally and acaricidally effective amount of a compound of the formula:

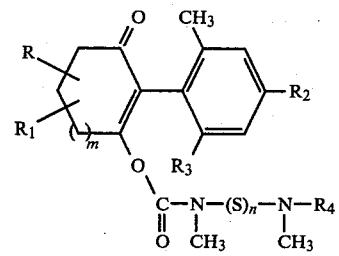

wherein:
m=0 or 1;
n=1 or 2;
R, R1, R2, and R3 are individually hydrogen or alkyl groups of one to four carbon atoms;
R4 is:
(a) fluorocarbonyl or
(b) a group of the formula:

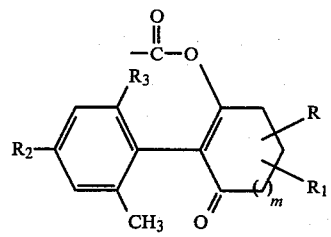

wherein R, R1, R2, R3 and m have the above indicated values;

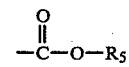

wherein R5 is:
(1) a phenyl group which is unsubstituted or substituted with one or more C1–C12 alkyl, chloro, fluoro, bromo, alkoxy, alkylthio, alkylthioalkyl, alkylsulfinyl, alkylsulfinylalkyl, alkylsulfonyl, alkylsulfonylalkyl, alkynyloxy, dialkylamino, alkoxyamino, formamidino, cyano, dioxolanyl or dithiolanyl group in any combination; or
(2) a naphthyl, tetrahydronaphthyl, dihydrobenzofuranyl, benzodioxalanyl, or benzothienyl group, all of which is unsubstituted or substituted with one or more alkyl groups; or
(3) a group of the formula:

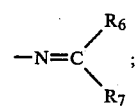

wherein R6 is a chloro, alkyl, alkylthio, cyanoalkylthio, amidoalkylthio or cyano group; or R6 is hydrogen provided R7 is not hydrogen;
R7 is an alkyl, alkylthio, alkoxycarbonyl, aminocarbonyl, alkylaminocarbonyl, dialkylaminocarbonyl, alkylthioalkyl, cyanoalkyl, alkylsulfinylalkyl, alkylsulfonylalkyl, alkoxyalkyl, nitroalkyl, hydroxyalkyl, or phenyl group, said phenyl group is unsubstituted or substituted with one or more alkyl, chloro, or fluoro groups in any combination; or $R_7$ is hydrogen, provided $R_6$ is not hydrogen; or (4) cyclic oximes selected from the group consisting of 2-oximino-1,4-dithianes, 2-oximino-1,3-dithianes, 4-oximino-1,3-dithiolanes, 2-oximino-1,4-dioxanes, 2-oximino-tetrahydro-1,4-thiazine-3-ones, 2-oximino-1,3-dithiolanes, 2-imino-4-oximino-1,3-dithiolanes, 3-oximinothiophanes, 2-oximinothiophanes, 2-oximino-tetrahydro-1,4-oxazine-3-ones, 2-oximino-1,4-oxathianes, 4-oximino-1,3-oxathiolanes, 2-oximino-thiazolidin-3-ones, 2-oximino-1,3-thiazolidin-4-ones or 2-oximino-tetrahydro-1,4-thiazin-5-ones, each of which is unsubstituted or substituted with one to four alkyl groups and wherein sulfur can be in any of its oxidation states.

34. A method according to claim 33 wherein R, $R_1$, $R_2$ and $R_3$ are individually hydrogen, methyl and isopropyl.

35. A method according to claim 33 wherein $R_6$ is hydrogen, lower alkyl and alkylthio.

36. A method according to claim 33 wherein $R_7$ is lower alkyl, alkylthioalkyl, cyanoalkyl and alkylsulfonylalkyl.

37. A method of controlling insects and acarids which comprises subjecting them to an insecticidally and acaricidally effective amount of a compound of the formula:

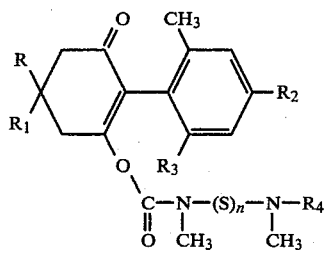

wherein:
n=1 or 2;
R, $R_1$ and $R_2$ are individually hydrogen or alkyl groups of one to four carbon atoms;
$R_3$ is hydrogen;
$R_4$ is:
(a) fluorocarbonyl or
(b) a group of the formula:

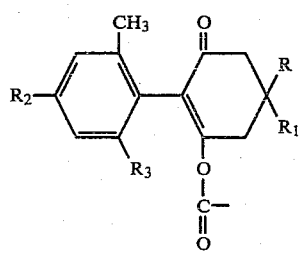

wherein R, $R_1$, $R_2$, and $R_3$ have the above indicated values;

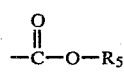

wherein $R_5$ is:
(1) a phenyl group which is unsubstituted or substituted with one or more $C_1$-$C_{12}$ alkyl, chloro, fluoro, bromo, alkoxy, alkylthio, alkylthioalkyl, alkylsulfinyl, alkylsulfinylalkyl, alkylsulfonyl, alkylsulfonylalkyl, alkynyloxy, dialkylamino, alkoxyamino, formamidino, cyano, dioxolanyl or dithiolanyl group in any combination; or (2) a naphthyl, tetrahydronaphthyl, dihydrobenzofuranyl, benzodioxolanyl, or benzothienyl group, all of which is unsubstituted or substituted with one or more alkyl groups; or (3) a group of the formula:

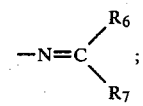

wherein $R_6$ is a chloro, alkyl, alkylthio, cyanoalkylthio, amidoalkylthio or cyano group; or $R_6$ is hydrogen provided $R_7$ is not hydrogen;

(3) $R_7$ is an alkyl, alkylthio, alkoxycarbonyl, aminocarbonyl, alkylaminocarbonyl, dialkylaminocarbonyl, alkylthioalkyl, cyanoalkyl, alkylsulfinylalkyl, alkylsulfonylalkyl, alkoxyalkyl, nitroalkyl, hydroxyalkyl, or phenyl group, said phenyl group is unsubstituted or substituted with one or more alkyl, chloro, or fluoro groups in any combination; or $R_7$ is hydrogen, provided $R_6$ is not hydrogen; or (4) cyclic oximes selected from the group consisting of 2-oximino-1,4-dithianes, 2-oximino-1,3-dithianes, 4-oximino-1,3-dithiolanes, 2-oximino-1,4-dioxanes, 2-oximino-tetrahydro-1,4-thiazine-3-ones, 2-oximino-1,3-dithiolanes, 2-imino-4-oximino-1,3-dithiolanes, 3-oximinothiophanes, 2-oximinothiophanes, 2-oximinotetrahydro-1,4-oxazine-3-ones, 2-oximino-1,4-oxathianes, 4-oximino-1,3-oxathiolanes, 2-oximino-thiazolidin-3-ones, 2-oximino-1,3-thiazolidin-4-ones or 2-oximino-tetrahydro-1,4-thiazin-5-ones, each of which is unsubstituted or substituted with one to four alkyl groups and wherein sulfur can be in any of its oxidation states.

38. A method according to claim 37 wherein R, $R_1$ and $R_2$ are individually hydrogen, methyl and isopropyl.

39. A method according to claim 37 wherein $R_6$ is hydrogen, lower alkyl and alkylthio.

40. A method according to claim 37 wherein $R_7$ is lower alkyl, alkylthioalkyl, cyanoalkyl and alkylsulfonylalkyl.

41. A method according to claim 37 wherein R, $R_1$ and $R_2$ are individually hydrogen, methyl and isopropyl;
$R_6$ is hydrogen, lower alkyl and alkylthio;
$R_7$ is lower alkyl, alkylthioalkyl, cyanoalkyl and alkylsulfonylalkyl.

42. A method according to claim 37 wherein the compound is 1-[N-Methyl-N-[N'-methyl-N'-methyl-N'-fluorocarbonylaminosulfenyl]carbamoyloxy]-2-(2'-methylphenyl)-5,5-dimethyl-1-cyclohexene-3-one.

43. A method according to claim 37 wherein the compound is 1-[N-Methyl-N-[N]-methyl-N'-fluorocarbonylaminosulfenyl]carbamoyloxy]-2-(2',4'-dimethylphenyl)-5,5-dimethyl-1-cyclohexene-3-one.

44. A method according to claim 37 wherein the compound is S-Methyl-N-[N'-[N''-methyl-N''-[1-(2-

(2',4'-dimethylphenyl)-5,5-dimethyl-1-cyclohexene-3-one)oxycarbonyl]aminosulfenyl]-N'-methylcarbamoyloxy]acetimidate.

45. A method according to claim 37 wherein the compound is 1-[N-methyl-N-[N'-methyl-N'-[1-(2-(2'-methylphenyl)-5,5-dimethyl-3-oxo-1-cyclohexenyl)oxycarbonyl]aminosulfenyl]carbamoyloxy]naphthalene.

46. A method according to claim 37 wherein the compound is 7-[N-methyl-N-[N'-methyl-N'-[1-(2-(2',4'-dimethylphenyl)-5,5-dimethyl-3-oxo-1-cyclohexenyl)oxycarbonyl]aminosulfenyl]carbamoyloxy]-2,2-dimethyl-2,3-dihydrobenzofuran.

47. A method according to claim 37 wherein the compound is 4-[N-methyl-N-[N'-methyl-N'-[1-(2-(2',4'-dimethylphenyl-5,5-dimethyl-3-oxo-1-cyclohexenyl)oxycarbonyl]-2,2-dimethylbenzodioxolan.

48. A method according to claim 37 wherein the compound is S-Methyl-N-[N'-[N''-methyl-N''-[1-(2-(2',4'-dimethylphenyl)-5-isopropyl-1-cyclohexene-3-one)oxycarbonyl]aminosulfenyl]-N'-methylcarbamoyloxy]acetimidate.

* * * * *